US010524719B2

(12) United States Patent
Palaniswami et al.

(10) Patent No.: US 10,524,719 B2
(45) Date of Patent: Jan. 7, 2020

(54) SYSTEM AND METHOD FOR IDENTIFICATION OF NEURO-CARDIOLOGICAL DISTURBANCES

(71) Applicant: NEUROANALYTICS PTY. LTD., Brighton (AU)

(72) Inventors: Marimuthu Palaniswami, Kew (AU); Jayavardhana Rama Gubbi Lakshminarasimha, Bangalore (IN)

(73) Assignee: NEUROANALYTICS PTY. LTD, Brighton, Vic (AU)

( * ) Notice: Subject to any disclaimer, the term of this patent is extended or adjusted under 35 U.S.C. 154(b) by 8 days.

(21) Appl. No.: 15/685,946

(22) Filed: Aug. 24, 2017

(65) Prior Publication Data
US 2018/0333094 A1 Nov. 22, 2018

(30) Foreign Application Priority Data
May 22, 2017 (AU) .................... 2017203433

(51) Int. Cl.
*A61B 5/00* (2006.01)
*A61B 5/11* (2006.01)
(Continued)

(52) U.S. Cl.
CPC .......... *A61B 5/4064* (2013.01); *A61B 5/0006* (2013.01); *A61B 5/02055* (2013.01);
(Continued)

(58) Field of Classification Search
CPC ... A61B 5/4064; A61B 5/0402; A61B 5/0452; A61B 5/1122; A61B 5/1123;
(Continued)

(56) References Cited

U.S. PATENT DOCUMENTS

2008/0001735 A1* 1/2008 Tran .................... G06F 19/3418
340/539.22
2010/0063365 A1* 3/2010 Pisani .................. A61B 5/0002
600/301
(Continued)

*Primary Examiner* — Catherine M Voorhees
(74) *Attorney, Agent, or Firm* — Symbus Law Group, LLC; Clifford D. Hyra (57) ABSTRACT

A system for identification of one or more neuro-cardiological disturbances of a subject in a post-acute stroke treatment and in the intensive care setting is provided. The system includes a wearable device configured for capturing data associated with a neural and heart activity. The wearable device includes a first electrode and a second electrode configured for measuring an electrical activity of a heart to generate a first signal. The wearable device also includes an accelerometer configured for detecting and acquiring neural accelerometry data to generate a second signal. Moreover, the system includes a processor with a memory. The memory stores a plurality of modules to be executed by the processor and wherein the plurality of modules are configured to receive the first and the second signal from the wearable device, combine the first signal and the second signal to generate an output signal, display the output signal, wherein the output signal is a graphical representation of a time-series data depicting one or more frequencies of the neural and heart activity and identify one or more neuro-cardiological disturbances based on the displayed output signal.

17 Claims, 5 Drawing Sheets

(51) Int. Cl.
    *A61B 5/0402*     (2006.01)
    *A61B 5/0452*     (2006.01)
    *A61B 5/0205*     (2006.01)
    *A61B 5/0404*     (2006.01)
    *A61B 5/0408*     (2006.01)
    *A61B 5/044*     (2006.01)
    *A61B 5/024*     (2006.01)

(52) U.S. Cl.
    CPC .......... *A61B 5/0402* (2013.01); *A61B 5/0404* (2013.01); *A61B 5/044* (2013.01); *A61B 5/0452* (2013.01); *A61B 5/04085* (2013.01); *A61B 5/11* (2013.01); *A61B 5/1122* (2013.01); *A61B 5/1123* (2013.01); *A61B 5/4076* (2013.01); *A61B 5/4094* (2013.01); *A61B 5/4519* (2013.01); *A61B 5/681* (2013.01); *A61B 5/6824* (2013.01); *A61B 5/02416* (2013.01); *A61B 5/726* (2013.01); *A61B 5/7221* (2013.01); *A61B 5/7246* (2013.01); *A61B 2560/0247* (2013.01); *A61B 2562/0219* (2013.01)

(58) Field of Classification Search
    CPC ... A61B 5/6824; A61B 5/4094; A61B 5/4076; A61B 5/04085; A61B 5/0404; A61B 5/02055; A61B 5/11; A61B 5/0006; A61B 5/4519; A61B 5/044; A61B 5/681
    See application file for complete search history.

(56) References Cited

U.S. PATENT DOCUMENTS

2011/0224602 A1*   9/2011   Struijk ............... A61B 5/04001
    604/66
2014/0275854 A1*   9/2014   Venkatraman ......... A61B 5/721
    600/301

* cited by examiner

SYSTEM AND METHOD FOR IDENTIFICATION OF NEURO-CARDIOLOGICAL DISTURBANCES

This non-provisional application claims priority to Australian Application No. 2017203433 filed May 22, 2017, which is incorporated herein by reference in its entirety.

FIELD OF TECHNOLOGY

This disclosure relates generally to systems and methods for monitoring a person in post-acute stroke period and in the intensive care unit, and more particularly to a system and method for identification of one or more neuro-cardiological disturbances in a person in post-acute stroke period and in the intensive care unit.

BACKGROUND

Acute stroke affects more than of about 6.2 million patients per annum on a global scale. A significant proportion, approximately twenty five percent, of stroke patients demonstrates neurological (brain) deterioration either concurrently or independently of heart rhythm disturbances. Neurological deterioration and heart rhythm (cardiac arrhythmia) disturbances are associated with increased morbidity and mortality. However, if neurological deterioration or cardiac arrhythmia is detected early, an opportunity for medical or surgical intervention exists, the expedited treatment of which will likely lead to improved outcomes.

The monitoring of brain function deterioration and heart rhythm disturbances (termed cardiac arrhythmia) requires frequent nursing observations and assessments (e.g. neurological examination and pulse examination). The current clinical practice for monitoring cardiac arrhythmia in stroke patients stipulate 2 to 3 assessments per day. However, neurological deterioration and cardiac arrhythmia are paroxysmal in nature and often occur in stroke patients without any warnings. It follows that current frequency of monitoring of stroke patients is prone to delayed diagnosis, leading to missed opportunities for medical and surgical intervention.

Currently, the patients are admitted in intensive care unit (ICU) when they have stroke or other cardio-vascular ailments. The patient could be in comatose state or non-comatose state. They end up spending significant time in intensive care unit (ICU) or other critical care scenarios. However, abnormal muscular activities pertaining to stroke patients need to be identified and treated at an early stage. It is found that aggressive physiotherapy with patients ensures quicker recovery after discharge. For this to be actionable, the doctor or the physiotherapist needs to have full knowledge regarding the condition of patient limbs which provide indirect but measurable markers of neural activity.

SUMMARY

In order to solve at least some of the above mentioned problems, there exists a need for a system and method that monitors muscle activity in patients with cardio vascular disease and other diseases. A system and method is needed for monitoring heart and brain activity that captures the motor activity of brain that is an indirect indicator of neural activity.

Example embodiments provide a system for identifying one or more neuro-cardiological disturbances. The system includes a wearable device configured for capturing data associated with a neural and heart activity. The wearable device includes a first electrode and a second electrode configured for measuring an electrical activity of a heart to generate a first signal. The wearable device also includes an accelerometer configured for detecting and acquiring neural accelerometry data to generate a second signal. Moreover, the system includes a processor with a memory. The memory stores a plurality of modules to be executed by the processor and wherein the plurality of modules are configured to receive the first and the second signal from the wearable device, combine the first signal and the second signal to generate an output signal, display the output signal, wherein the output signal is a graphical representation of a time-series data depicting one or more frequencies of the neural and heart activity and identify one or more neuro-cardiological disturbances based on the displayed output signal.

According to yet another example embodiment, a method for identifying one or more neuro-cardiological disturbances is provided. The method includes capturing data associated with a neural and heart activity in a post-acute stroke treatment. The steps for capturing data associated with the neural and heart activity include measuring an electrical activity of a heart to generate a first signal and detecting and acquiring neural accelerometry data to generate a second signal. The method further includes receiving the first and the second signal and combining the first signal and the second signal to generate an output signal. In addition, the method includes displaying the output signal, wherein the output signal is a graphical representation of a time-series data depicting one or more frequencies of the neural and heart activity. The method also includes identifying one or more neuro-cardiological disturbances based on the displayed output signal.

The above summary is illustrative only and is not intended to be in any way limiting. In addition to the illustrative aspects, example embodiments, and features described above, further aspects, example embodiments, and features will become apparent by reference to the drawings and the following detailed description.

BRIEF DESCRIPTION OF THE FIGURES

These and other features, aspects, and advantages of the exemplary embodiments can be better understood when the following detailed description is read with reference to the accompanying drawings in which like characters represent like parts throughout the drawings, wherein:

FIG. 2-A illustrates a broad level architecture of system of FIG. 1 for monitoring a patient in post-acute stroke period and in the intensive care setting, for identification of one or more neuro-cardiological disturbances, according to an embodiment of the present disclosure;

FIG. 2-B illustrates an exploded view of a wearable device of FIG. 1 comprising a plurality of sensors and other components, according to an embodiment of the present disclosure;

Further, skilled artisans will appreciate that elements in the figures are illustrated for simplicity and may not have necessarily been drawn to scale. Furthermore, in terms of the construction of the device, one or more components of the device may have been represented in the figures by conventional symbols, and the figures may show only those specific details that are pertinent to understanding the embodiments of the present invention so as not to obscure the figures with details that will be readily apparent to those of ordinary skill in the art having the benefit of the description herein.

DETAILED DESCRIPTION

For the purpose of promoting an understanding of the principles of the invention, reference will now be made to the embodiments illustrated in the figures and specific language will be used to describe the same. It will nevertheless be understood that no limitation of the scope of the invention is thereby intended, such alterations and further modifications in the illustrated system, and such further applications of the principles of the invention as illustrated therein being contemplated as would normally occur to one skilled in the art to which the invention relates.

It will be understood by those skilled in the art that the foregoing general description and the following detailed description are exemplary and explanatory of the invention and are not intended to be restrictive thereof.

The terms "comprises", "comprising", or any other variations thereof, are intended to cover a non-exclusive inclusion, such that a process or method that comprises a list of steps does not comprise only those steps but may comprise other steps not expressly listed or inherent to such process or method. Similarly, one or more devices or sub-systems or elements or structures or components proceeded by "comprises . . . a" does not, without more constraints, preclude the existence of other devices or other sub-systems or other elements or other structures or other components or additional devices or additional sub-systems or additional elements or additional structures or additional components. Appearances of the phrase "in an embodiment", "in another embodiment" and similar language throughout this specification may, but do not necessarily, all refer to the same embodiment.

Unless otherwise defined, all technical and scientific terms used herein have the same meaning as commonly understood by one of ordinary skill in the art to which this invention belongs. The system, methods, and examples provided herein are illustrative only and not intended to be limiting.

At least one exemplary embodiment is generally directed towards methods and systems for monitoring a person in post-acute stroke period and identification of one or more neuro-cardiological disturbances of a person in a post-acute stroke treatment and in the intensive care setting. Exemplary embodiments provide a system and method that monitors muscle activity in patients with cardio vascular disease and other diseases. For conciseness, a method and system for identification of one or more neuro-cardiological disturbances in a person in post-acute stroke period and in the intensive care setting is provided.

Some embodiments may relate to a system for identifying one or more neuro-cardiological disturbances. The system includes a wearable device configured for capturing data associated with a neural and heart activity. The wearable device includes a first electrode and a second electrode configured for measuring an electrical activity of a heart to generate a first signal. The wearable device also includes an accelerometer configured for detecting and acquiring neural accelerometry data to generate a second signal. Moreover, the system includes a processor with a memory. The memory stores a plurality of modules to be executed by the processor and wherein the plurality of modules are configured to receive the first and the second signal from the wearable device, combine the first signal and the second signal to generate an output signal, display the output signal, wherein the output signal is a graphical representation of a time-series data depicting one or more frequencies of the neural and heart activity and identify one or more neuro-cardiological disturbances based on the displayed output signal.

Some descriptions herein may relate to a method for identifying one or more neuro-cardiological disturbances in a person in post-acute stroke period. The method includes capturing data associated with a neural and heart activity of the patient in a post-acute stroke treatment. The steps for capturing data associated with the neural and heart activity include measuring an electrical activity of the heart to generate a first signal and detecting and acquiring neural accelerometry data to generate a second signal. The method further includes receiving the first and the second signal and combining the first signal and the second signal to generate an output signal. In addition, the method includes displaying the output signal, wherein the output signal is a graphical representation of a time-series data depicting one or more frequencies of the neural and heart activity. The method also includes identifying one or more neuro-cardiological disturbances based on the displayed output signal. Examples of one or more neuro-cardiological disturbances include, but are not limited to critical care myopathy, critical care polyneuropathy, delirium, hypoxic myoclonus, encephalitis, encephalopathy, systemic inflammatory response syndrome, status epilepticus or combinations thereof.

Example embodiments described herein relate to hybrid heart and brain monitoring system. Moreover, a patient activity monitoring system for intensive care unit (ICU) and coronary care unit (CCU) is provided.

In addition to the illustrative aspects, exemplary embodiments, and features described above, further aspects, exemplary embodiments of the present disclosure will become apparent by reference to the drawings and the following detailed description.

Figure 1:
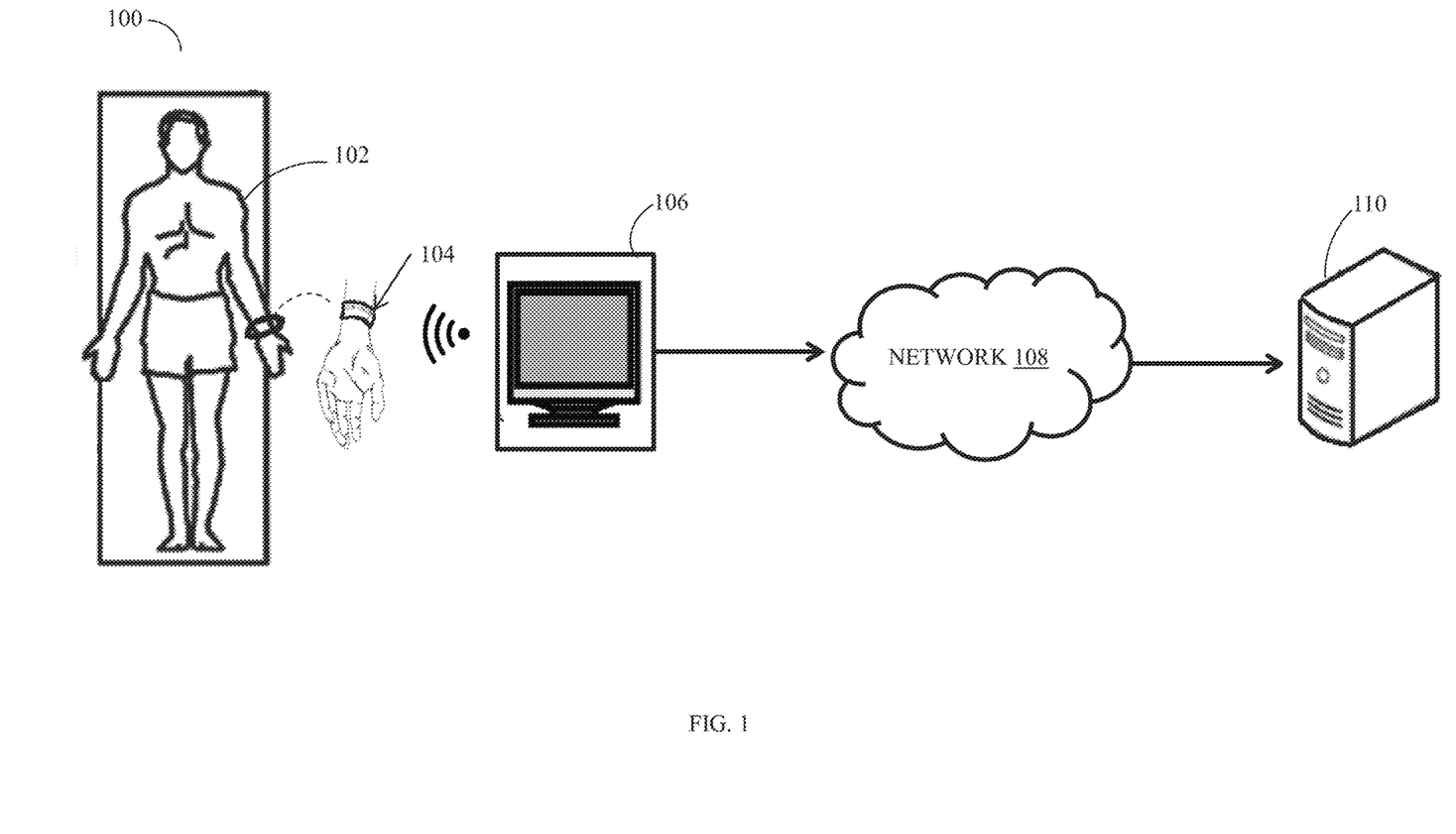
FIG. 1 illustrates one embodiment of a system configured for monitoring a patient in post-acute stroke period and in the intensive care setting, for identification of one or more neuro-cardiological disturbances, according to an embodiment of the present disclosure.

FIG. 1 illustrates one embodiment of a system 100 configured for monitoring a patient in post-acute stroke period and in the intensive care setting, for identification of one or more neuro-cardiological disturbances, according to an embodiment of the present disclosure. In particular, FIG. 1 comprises a subject (patient) 102, a wearable device 104, a data collector device 106, a network 108, and a data processing unit 110. Each component is described in further details below.

The system 100 may be configured to operate at a home, a nursing home, or a hospital. The patient 102 may also be referred as a 'subject' and the term 'patient' and 'subject' may be used interchangeably in the description below. In one embodiment, the patients may be persons with cardio vascular disease and other diseases. They may be admitted in ICU. In one example embodiment, they may have stroke or other cardio-vascular ailments. The patient may be in comatose state or non-comatose state.

In one embodiment, the wearable device 104 may be patient monitoring device that can be worn by the patient. The wearable device 104 comprise two main components. The two components include a heart activity monitoring unit and a neural activity monitoring unit.

The heart activity monitoring unit of the wearable device 104 is configured to detect physiological parameters and convert them to usable heart rate reading. The heart activity monitoring unit of the wearable device 104 may be a Heart Rate Monitor (HRM) which is an electronic device that detects physiological parameters and converts them to usable heart rate reading. Heart rate is the number of times the heart beats in a minute and it is produced via depolarization at the sinoatrial and atrioventricular nodes in the heart. Examples of available HRM's include, but are not limited to a sensing probe attached to a patient's earlobe, toe, finger or other body locations, depending upon the sensing method (reflection or transmission), and a data acquisition system for the calculation and eventually display of the heart rate. However, the heart activity monitoring unit of the wearable device 104 as described herein is configured for achieving a low power, portable, low-end reflectance mode wrist based HRM (wearable device 104).

The neural activity monitoring unit of the wearable device 104 is configured to capture the motor activity of the brain that is an indirect indicator of neural activity. In one example embodiment, the wearable device 104 may be a sensor. The wearable device 104 may comprise a plurality of sensors configured for sensing data associated with the neural and heart activity of the patient 102 in a post-acute stroke treatment.

The heart activity monitoring unit of the wearable device 104 includes a first electrode and a second electrode configured for measuring an electrical activity of the heart of the patient to generate a first signal. The first electrode is placed at an under surface of the wearable device 104 and adjacent to the radial artery of the subject 102 permitting direct contact with a subject's ipsilateral wrist who is wearing the wearable device 104. The second electrode is placed on the outer surface of the wearable device 104 permitting direct contact with the subject's contralateral hand. The second electrode is exposed on the outer side of the wearable device 104. The subject needs to place his/her index finger on this second electrode that may assist in identifying the pulse.

The first electrode and the second electrode is configured to collect signals from the subject 102. In one embodiment, the signals may be associated with electrical activity of the subject's heart. The signals collected from the first electrode and the second electrode are combined using an algorithm to generate an ECG waveform. In one embodiment, the algorithm implemented for combining the signals collected from the first electrode and second electrode is configured for heart rhythm abnormality detection based on filter bank approach (described in detail below).

The neural activity monitoring unit of the wearable device 104 includes an accelerometer configured for detecting and acquiring neural accelerometry data to generate a second signal. In one embodiment, the neural activity monitoring unit of the wearable device 104 includes an in-built accelerometer configured to automatically detect and perform acquisition of wrist accelerometer data. The acquired wrist accelerometry data acts as a surrogate marker for brain function post stroke. Further, the accelerometer is configured to measure muscular activity. In one example embodiment, the accelerometers are motion sensors such as, gyroscopes, and magnetometers that help to identify whether a person is seated, walking, or running. The accelerometer is configured to identify the orientation of the arm, wrist, or other specific part of the subject's body where the activity monitor is located. In one embodiment, the functioning of accelerometer is described in detail in PCT application PCT/AU2015/000725 entitled "System And Method For Monitoring Motor Recovery in a Post Acute Stroke Treatment" filed on the Dec. 1, 2015," the entire content of which is incorporated herein by reference.

In one example embodiment, the signals sensed (captured) by the first electrode and second electrode of the wearable device 104 are first filtered for movement artefact using the accelerometer data and converted into time series data. This time series data may be similar to ECG data with PQRSTU waveform but will lack the details. In one example embodiment, the PQRSTU waveform illustrates the P wave, QRS complex and the T wave represent electrical activity in the heart on an electrocardiogram. The ECG Learning Center explains that the P wave represents the depolarization of the right and left atria. The QRS complex follows the P wave and depicts the activation of the right and left ventricles. For example, the practical clinical skills reveals that the T wave indicates repolarization of the ventricles.

The time series data may be highly correlated with poly plethysomography data. Further, the cardiac abnormality is detected from the new data. Many algorithms exists to do this from ECG data but the data collected by the wearable device 104 is unique and appears different. As a result, correlation of the time series data with accelerometer data is conducted to map into new space. An algorithm is implemented to generate index for deterioration, combining correlated data is conducted using hyper-conic clustering. Final classification is conducted using a Biased SVM model instead of simple threshold.

In one embodiment, in order to address comatose and non-comatose patient, a filter bank is created for automatic detection of one or more neuro-cardiological disorders. The data processing unit 110 comprises a memory and the processor. The memory comprises the filter bank consisting's of a plurality of frequencies in the range of about 1 Hertz to 1000 Hertz.

The processor is configured to analyze the accelerometry data to provide muscular activity data, based on which, the neural activity data is measured. Further, the processor is configured to convert the accelerometry data into one or more frequencies. The processor is configured to compare the converted one or more frequencies with the stored plurality of frequencies (stored in filter bank) to generate time-series data. The processor is configured to analyze the generated time-series data for automatic detection of one or more neuro-cardiological disorders for comatose and non-comatose subject. Example of one or more neuro-cardiological disorders automatically detected based on accelerometry data comprise critical care myopathy, critical care polyneuropathy, encephalitis, encephalopathy and status epilepticus or combinations thereof.

The filter bank approach ensures capturing and analyzing of all kinds of activities that include 'very low frequency', 'low frequency', 'as well as high frequency twitches'. An algorithm is implemented to convert this captured activity to equivalent recovery indices based on correlation of signals. The steps executed by the algorithm comprises the said steps. Firstly, the captured accelerometer data is pre-processed and time synchronization is achieved at the hardware level. Further, as mentioned in above paragraphs, a filter bank is designed to split the accelerometer data into different frequency ranges. Different frequency ranges are correlated with different types of movements including: seizure, tremor, Dyskinesia, Myoclonus, TIC. The signatures are collected in hospital setting. For detecting seizures and other repeated movement, a time-frequency analysis is conducted using wavelet filter banks method. A hyper conic clustering method is used for classification using Cauchy membership function. The clustering may assists in finding the anomalous data that is separated from normal data. The historical data is used and hence the algorithm is subject independent. Lastly, the correlation with NIHSS indices is carried out and specific markers are derived for acute stroke analysis.

The data collector device 106 may be configured for collecting the signals sensed by the wearable device 104. The data collector device 106 may be embedded in the wearable device 104 or may be situated outside the wearable device 104. In one embodiment, the data processing unit 110 may be situated at the ICU near the patient 102 or at some other location from the ICU.

When the data processing unit 110 is situated at some other location, other than ICU, the data processing unit 110 is configured to receive the first signal and the second signal from the data collector device 106 or directly from the wearable device 104. The data collector device 106 or the wearable device 104 is configured to transmit the first signal and the second signal to at least one base station and the at least one base station comprises a transceiver for receiving the first signal and the second signal. The first signal and the second signal are transmitted via the network 108. The network 108 may be a wireless network, a wired network or a combination thereof. The network 108 can be implemented as one of the different types of networks, such as intranet, local area network (LAN), wide area network (WAN), the internet, Bluetooth and the like. The network 108 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further the network 108 may include a variety of network devices, including routers, bridges, servers, computing devices, storage devices, and the like.

In one embodiment, the data processing unit 110 comprises a memory and a processor (not shown in FIGS). The memory stores a plurality of modules to be executed by the processor. In one embodiment, the processor is configured to combine the first signal and the second signal to generate an output signal. In one example embodiment, the combination of the first signal and the second signal illustrates combining the heart-brain activity. For example, an algorithm is implemented that can combine the first signal and the second signal. For conciseness, the first signal and the second signal are independent component. The algorithm may be based on higher-level data augmentation using a Bayesian process.

The output signal is displayed on a display device (not shown). The output signal is a graphical representation of a time-series data depicting one or more frequencies of the neural and heart activity. The one or more frequencies are utilized in acute stroke monitoring for the patient 102 with cardio vascular disease. In one embodiment, the processor is configured to identify one or more neuro-cardiological disturbances based on the displayed output signal. The processor is configured to analyze the output signal to identify one or more neuro-cardiological disorders. The one or more neuro-cardiological disorders comprise and are not limited to delirium, systemic or combinations thereof.

The manner in which the system 100 facilitates identification one or more neuro-cardiological disturbances for a patient in post-acute stroke period remotely is described in further detail below.

Figure 2A:
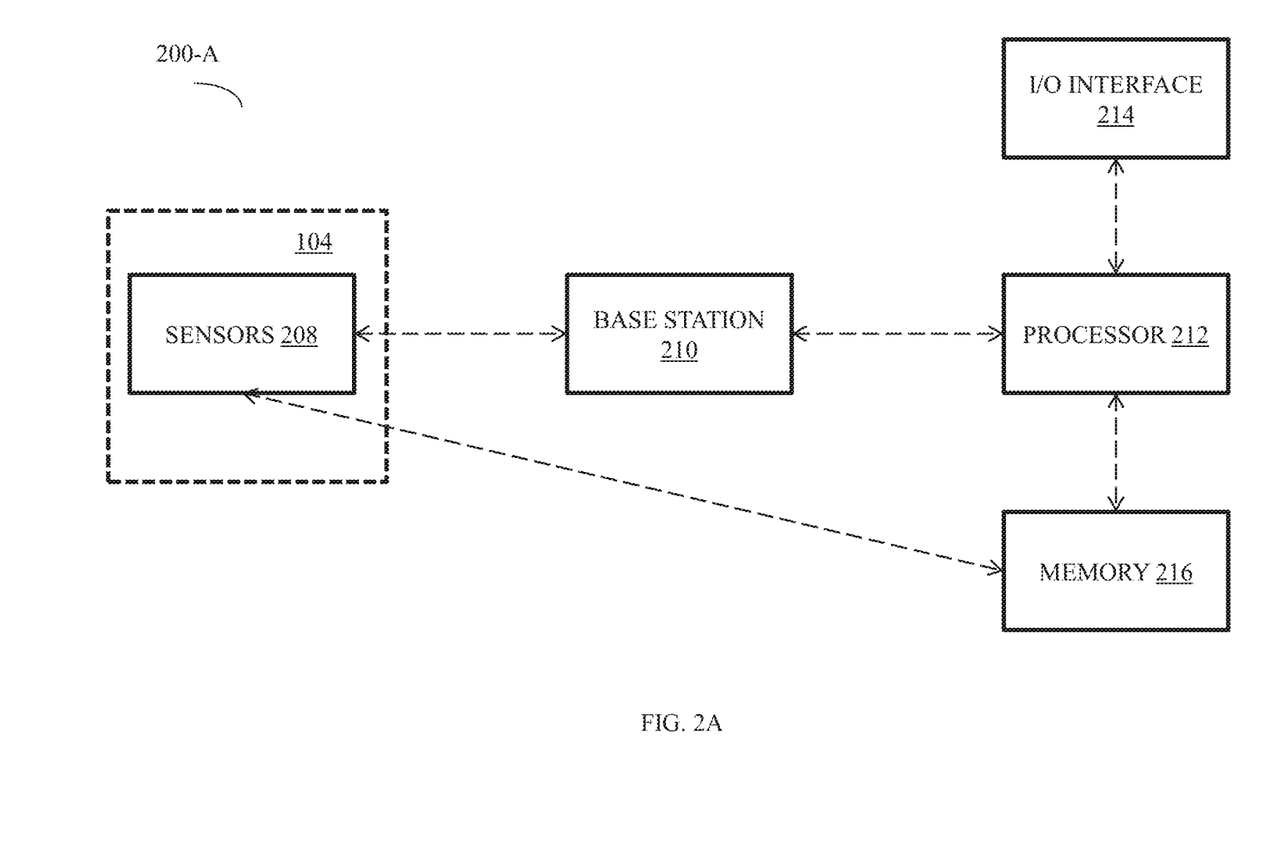
Figure 2B:
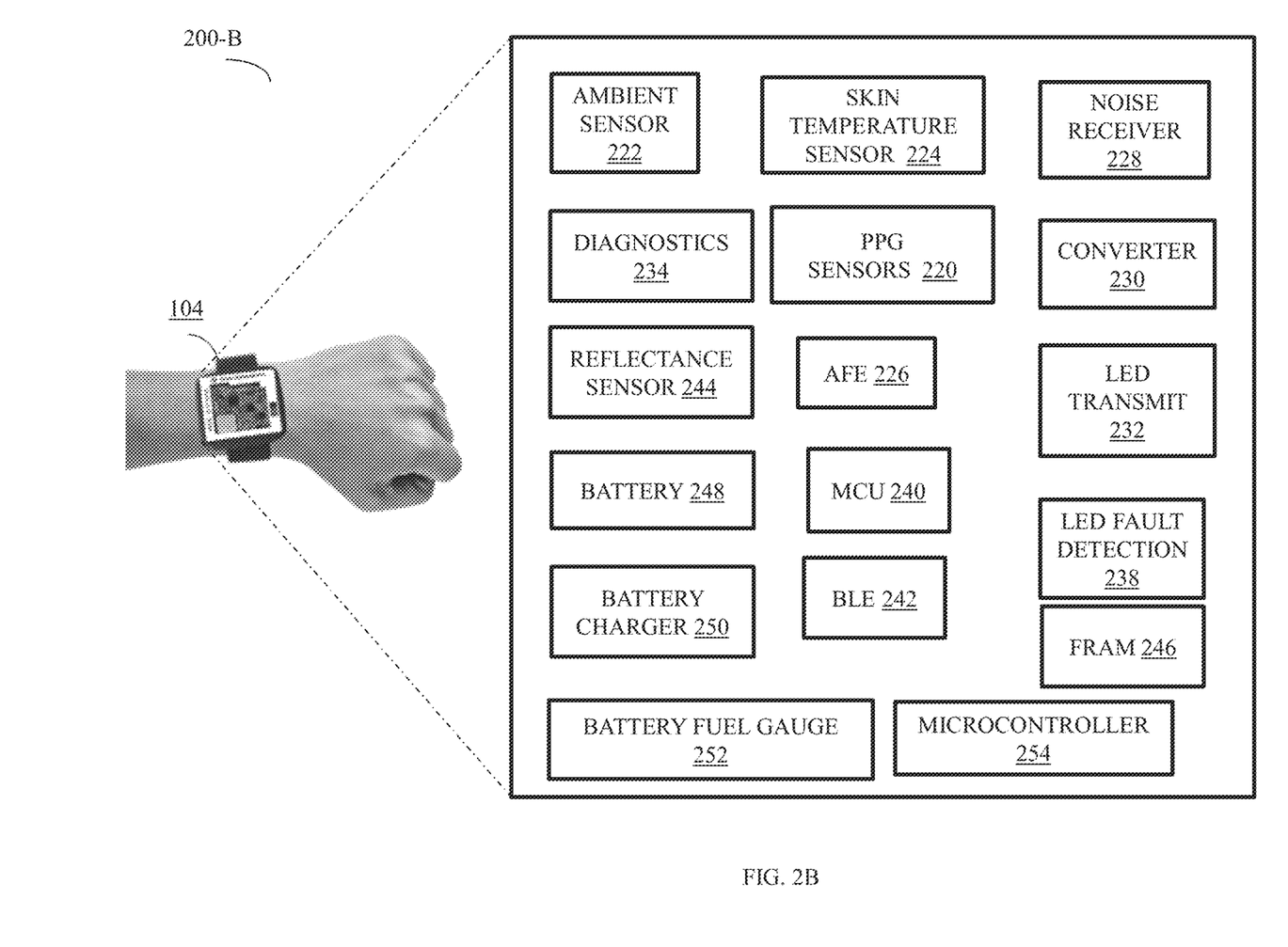

FIG. 2-A illustrates a broad level architecture 200-A of system of FIG. 1 for monitoring a patient in post-acute stroke period and in the intensive care setting, for identification of one or more neuro-cardiological disturbances, according to an embodiment of the present disclosure. Referring now to FIG. 2-A, the system 200-A, illustrates a wearable device 104 comprising a plurality of sensors 208, and a base station 210. The system 200-A also illustrates a processor 212 coupled to I/O interface 214 and a memory 216. In one embodiment, the wearable device 104 comprises a plurality of sensors (208) and other components, as shown in FIG. 2-B. FIG. 2-B illustrates an exploded view 200-B of a wearable device 104 of FIG. 1 comprising a plurality of sensors and other components as shown. In one example embodiment, the lower surface of the wearable device 104 includes photoplethysmography (PPG) sensors 220, the upper surface includes another PPG sensor (where index finger is placed). Further, the wearable device 104 has an ambient sensor measurement 222 on top and skin temperature measurement 224 at the bottom. The information sensed from PPG sensors are used for deriving cardiac activities. Temperature sensors are used for monitoring and making corrections to derived cardiac activities.

In one embodiment, the PPG sensor as part of the wearable device 104 and other sensors present in the wearable device 104 are used to derive a precise accurate signal (output signal), In one embodiment, the wearable device 104 employs reflectance mode photoplethysmography (PPG) to extract the pulse signal from the wrist of the subject 102 which is equivalent to the heart beat. In another embodiment, the wearable device 104 comprises a Fully Integrated Analog Front End (AFE) 226 that consists of a low noise receiver channel 228 with an integrated Analog to Digital Converter 230, an LED transmit section 232, diagnostics for sensor 234 and LED fault detection 238. Further, the wearable device 104 comprises additional components which are an ultra-low power microcontroller (MCU) 240 for calculating the heart rate, a wireless module based on Bluetooth Low Energy (BLE) 242 for exchanging information with smart phones, tablets or PCs, a motion sensor (accelerometer) for monitoring the user's activity, a reflectance mode sensing probe 244, ferroelectric RAM (FRAM) 246 for data logging, a lithium-polymer rechargeable battery 248, a battery charger 250 and a battery fuel gauge 252. Further, the wearable device 104 also includes a microcontroller 254 configured to calculate the heart rate, merge the motion sensor data, and process the AFE information. The microcontroller 254 is with specific features including the ability to maintain the context at all times. The microcontroller 254 also has a limited power budget because it has to continuously run for monitoring the subject to avoid drain of batteries.

The sensors 208 is configured for capturing data associated with a neural and a heart activity of the patient. The patient may be a person with cardio vascular disease and other diseases admitted in ICU. In one example embodiment, the patient may have stroke or other cardio-vascular ailments. The patient may be in comatose state or non-comatose state.

In one embodiment, the sensor 208 comprises a first electrode and a second electrode configured for measuring an electrical activity of the heart to generate a first signal. The sensor 208 also comprises an accelerometer configured for detecting and acquiring neural accelerometry data to generate a second signal. The processor 212 is configured to receive the first and the second signal from the wearable device. The processor 212 is configured to combine the first signal and the second signal to generate an output signal.

The system 200 may include at least one processor 212 (for both the sensor 208 and the base station 210), an input/output (I/O) interface 214 (herein a configurable user interface), a memory 216. The at least one processor 212 may be implemented as one or more microprocessors, microcomputers, microcontrollers, digital signal processors, central processing units, state machines, logic circuitries, and/or any devices that manipulate signals based on operational instructions. Among other capabilities, the at least one processor 212 is configured to fetch and execute computer-readable instructions stored in the memory 216.

The I/O interface 214 may include a variety of software and hardware interfaces, for example, a web interface, a graphical user interface, and the like. The output signal is displayed on a display device (214). The output signal is a graphical representation of a time-series data depicting one or more frequencies of the neural and heart activity. The processor 212 is configured to identify one or more neuro-cardiological disturbances based on the displayed output signal.

In one embodiment, each signal comprising the first signal, the second signal and the combined output signal is configured for automatic detection of one or more neuro-cardiological disorders for comatose and non-comatose subject.

In one example embodiment, the accelerometer data (i.e, the second signal) is configured for automatic detection of one or more neuro-cardiological disorders for comatose and non-comatose subject. Example of one or more neuro-cardiological disorders automatically detected based on accelerometry data comprise critical care myopathy, critical care polyneuropathy, encephalitis, encephalopathy and status epilepticus or combinations thereof In one example embodiment, for 'critical care myopathy', the symptoms shown by the patient include a kind of generalized muscle weakness after the patient has been lying in ICU for a few days, with both upper and lower limbs exhibiting decreased power. In such scenarios, the accelerometer data monitors physiology of the patient. For example, the accelerometer data measured by inbuilt accelerometry in the wearable device 104 indicates muscle activity and weakness, low power but activity more than sleep. As described, the captured accelerometer data is pre-processed and time synchronization is achieved at the hardware level. Further, as mentioned above in FIG. 1, a filter bank is designed to split the accelerometer data into different frequency ranges. When the processed accelerometer data provides, 'very little high frequency components', then it is concluded that the patient is indicating symptoms of 'critical care myopathy'.

In another example embodiment, for 'critical care polyneuropathy', the symptoms shown by the patient include a kind of generalized muscle weakness (but more than just muscle weakness as mentioned above for critical care myopathy') after the patient has been lying in ICU for a few days, with both upper and lower limbs exhibiting decreased power. In such scenarios, the accelerometer data monitors the patient. For example, the accelerometer data measured by inbuilt accelerometry in the wearable device 104 indicates muscle activity and weakness, low power but activity more than sleep. When the processed accelerometer data provides 'very little high frequency components' and when there exists 'low' intra class variation between the frequencies mentioned for 'critical care myopathy' and the frequencies for critical care polyneuropathy, an algorithm for differentiating is implemented. As per the algorithm, the filter bank divides the recorded signal, sensed by the wearable device, into multiple frequency bands. In one case, the frequencies are divided into bands comprising of about 15 Hz each. The different ICU elements manifests in different frequency bands with critical care polyneuropathy showing peaks in lower range frequency bands. This information is used to train a machine learning program, primarily a classifier (like a support vector machines or a neural networks) that will enable accurate detection of the type of weakness.

In another example embodiment, for 'encephalitis', the symptoms shown by the patient include infection or inflammation of the whole brain, patients exhibit motor twitches and jerks and occasionally seizures. In such scenarios, the accelerometer data monitors physiology of the patient. For example, the accelerometer data measured by inbuilt accelerometry in the wearable device 104 indicates muscle activity and weakness. When the processed accelerometer data illustrates high frequency jerks and repeated seizures as indicated by arm movement, then it is concluded that the patient is indicating symptoms of 'encephalitis'.

In another example embodiment, for 'encephalopathy' (usually caused by drugs or organ failure), the symptoms shown by the patient include motor twitches and jerks and sometimes seizures. In such scenarios, the accelerometer data monitors physiology of the patient. For example, the accelerometer data measured by inbuilt accelerometry in the wearable device 104 indicates muscle activity and weakness. When the processed accelerometer data illustrates 'Jerks' which are high frequency and the seizures are repeated arm movement, then it is concluded that the patient is indicating symptoms of 'encephalopathy'. This information such as 'Jerks' which are high frequency and the seizures' are captured by the higher range frequency bands in the filter bank. The filter bank divides the recorded signal into multiple frequency bands. In one case, the frequencies are divided into bands comprising of about 15 Hz each. The different ICU elements manifests in different frequency bands with encephalopathy showing peaks in lower range frequency bands. This information is used to train a machine learning program, primarily a classifier (like a support vector machines or a neural networks) that will enable accurate detection of the type of weakness.

In another example embodiment, for 'status epilepticus' the symptoms shown by the patient include ongoing, unstoppable seizures, the accelerometer data monitors physiology of the patient. For example, the accelerometer data measured by inbuilt accelerometry in the wearable device indicates muscle activity and weakness and seizures are repeated arm movement, then it is concluded that the patient is indicating symptoms of 'status epilepticus'.

In one example embodiment, the signals sensed (captured) by the first electrode and second electrode of the wearable device 104 are first filtered for movement artefact using the accelerometer data and converted into time series data. This time series data may be similar to ECG data with PQRSTU waveform but will lack the details. In one example embodiment, the PQRSTU waveform illustrates the P wave, QRS complex and the T wave represent electrical activity in the heart on an electrocardiogram. The ECG Learning Center explains that the P wave represents the depolarization of the right and left atria. The QRS complex follows the P wave and depicts the activation of the right and left ventricles. For example, the practical clinical skills reveals that the T wave indicates repolarization of the ventricles. The time series data may be highly correlated with poly plethysomography data. Further, the cardiac abnormality is detected from the new data. Many algorithms exists to do this from ECG data but the data collected by the wearable device 104 is unique and appears different. As a result, correlation with accelerometer data is conducted to map into new space. In one embodiment, an algorithm is implemented to generate index for deterioration, combining correlated data is conducted using hyper-conic clustering. Final classification is conducted using a Biased SVM model instead of a simple threshold. The time series data is the output signal. It is a multi-class classification that may be achieved using a simple threshold or a more sophisticated non-linear classification methods such as Radial Basis Function Neural Network, Support Vector Machine with Radial Basis Function kernel or a deep machine learning.

In one embodiment, as mentioned above in FIG. 1, the processor 212 is configured to identify one or more neuro-cardiological disturbances based on the displayed output signal. The processor 212 is configured to analyze the output signal to identify one or more neuro-cardiological disturbances for the one or more neuro-cardiological disorders. The one or more neuro-cardiological disorders comprise and are not limited to delirium, systemic inflammatory response syndrome or combinations thereof.

In one example embodiment, for identifying neuro-cardiological disorder such as 'Delirium', (the prediction of the problem using ECG), the symptoms shown by the patient include variations in heart rate. In this embodiment, a step is performed to derive heart rate from lower surface sensor and upper index finger sensor. The information from these sensors are intelligently combined using advanced sampling algorithm to reconstruct heart activity that correlates to polyplethysmography (PPG) waveform.

The signal from first electrode and from (second) upper electrode (where index finger is placed) is used as indicative of Delirium. In such scenarios, the physiology of the patient is being monitored. For example, the two polyplethysmography signal data and the heart activity data measured by the wearable device and combined using an algorithm as mentioned above, indicates primarily cardiac activity. Simultaneous measurement of muscular activity is also conducted.

In another example embodiment, the system of the present disclosure is configured for monitoring the one or more physiological parameters for predicting a neuro-cardiological disorder such as a generalized or focal hypoxic myoclonus. Specifically, the output signal from the wearable device 104 which is the combination of first signal sensed from electrodes and the second signal sensed from one or more accelerometers is processed at the base station 210 by using one or more algorithms described above to identify a general weakness or a cardiac arrest along with a generalized or focal muscle activity to predict the type of hypoxic myoclonus.

In another example embodiment, for systemic inflammatory response syndrome (total multi organ failure, the worst kind of encephalopathy), the sensors used are accelerometer and HRM (first electrode and second electrode). In such scenarios, the physiology of the patient is being monitored. For example, the output signal which is the combination of first signal sensed from electrodes and the second signal sensed from accelerometer indicates muscle activity and weakness, then it is concluded that the patient is indicating symptoms of 'systemic inflammatory response syndrome'.

Thus, it is seen that the signals sensed by the wearable device 104 (or the sensors 208) alone or in combination may be utilized to identify one or more neuro-cardiological disorders comprise critical care myopathy, critical care polyneuropathy, delirium, hypoxic myoclonus, encephalitis, encephalopathy, systemic inflammatory response syndrome, status epilepticus or combinations thereof.

The I/O interface 214 may allow the system 200 to transmit and receive data and commands to or from the base station 210. Further, the I/O interface 214 may enable the system 200 to communicate with other computing devices, such as web servers and external data servers (not shown). The I/O interface 214 can facilitate multiple communications within a wide variety of networks and protocol types, including wired networks, for example, LAN, cable, etc., and wireless networks, such as WLAN, cellular, or satellite. The I/O interface 214 may include one or more ports for connecting a number of devices to one another or to another server.

The memory 216 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The memory 206 may include modules (not shown in Figure) and may store The modules (although not shown in Figure) include routines, programs, objects, components, data structures, etc., which perform particular tasks, functions or implement particular abstract data types.

In accordance with an embodiment, the sensor 208 comprises a 3-axis accelerometer, a 3-axis Gyroscope, and a GPS sensor. The system 200 further comprises a digital signal processor, a transmitter (antenna or transceiver) with a TX buffer and a power supply unit. Referring to the base station 210, the sensor node 208 comprises a receiver with an RX buffer for encoding limbs movement data so filtered during the sensing. The microcontroller calculates the activity and stores the activity over a computer in a local database for providing a real-time visualization of stroke output. The base station 210 may also comprise a transceiver for transmitting and receiving the limbs movement data and commands.

Figure 3:
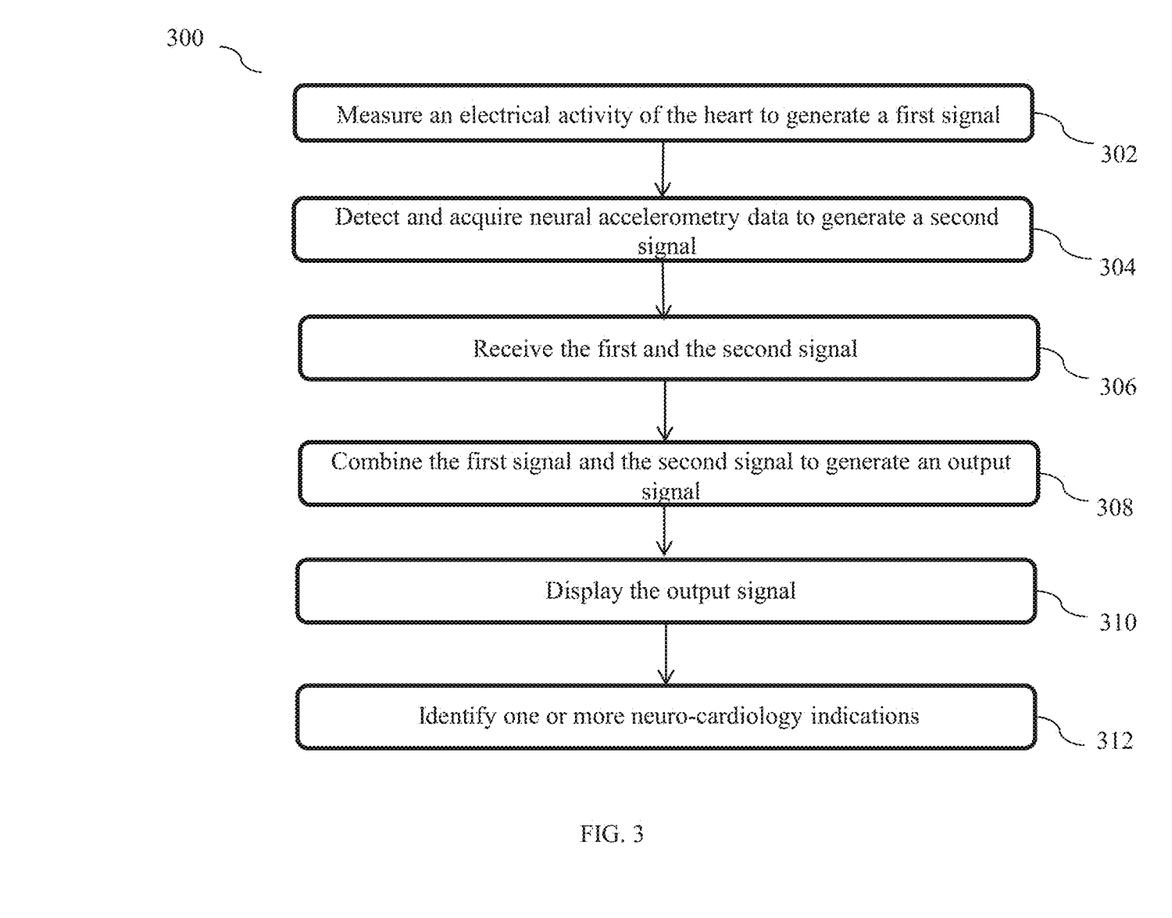
FIG. 3 is a flow chart illustrating a process for identifying one or more neuro-cardiological disturbances using the system of FIG. 1, according to an embodiment of the present disclosure.

FIG. 3 is a flow chart illustrating a process 300 for identifying one or more neuro-cardiological disturbances using the system of FIG. 1, according to an embodiment of the present disclosure. FIG. 3 will be described from the perspective of a processor (processor 212) that is configured to execute computer-readable instructions to carry out the functionalities of the above-described modules of the system 100 shown in FIG. 1. Each step is described in detail below.

At step 302, an electrical activity of a heart to generate a first signal is measured. At step 304, neural accelerometry data is detected and acquired to generate a second signal. At step 306, the first and second signal is received. At step 308, the first signal and the second signal are combined to generate an output signal. At step 310, the output signal is displayed. At step 312 one or more neuro-cardiological disturbances are identified.

In some embodiments, with reference to step 302, a heart activity monitoring unit of a wearable device (104 of FIG. 1) includes a first electrode and a second electrode configured for measuring an electrical activity of the heart of the patient to generate a first signal. The first electrode is placed at an under surface of the wearable device 104 and adjacent to the radial artery of the subject 102 permitting direct contact with a subject's ipsilateral wrist who is wearing the wearable device 104. The second electrode is placed on the outer surface of the wearable device 104 permitting direct contact with the subject's contralateral hand. The second electrode is exposed on the outer side of the wearable device 104. The subject needs to place his/her index finger on this second electrode that may assist in identifying the pulse. In one embodiment, the signals measured by the first electrode and the second electrode may be associated with electrical activity of the subject's heart. The signals collected from the first electrode and the second electrode are combined using an algorithm to generate an ECG waveform.

In some embodiments, with reference to step 304, the wearable device 104 also includes an accelerometer configured for detecting and acquiring neural accelerometry data to generate a second signal. In one embodiment, the neural activity monitoring unit of the wearable device 104 includes an in-built accelerometer configured to automatically detect and perform acquisition of wrist accelerometry data. The acquired wrist accelerometry data acts as a surrogate marker for brain function post stroke. In one embodiment, in order to address comatose and non-comatose patient, a filter bank is created (stored in the memory) for automatic detection of one or more neuro-cardiological disorders. The processor 212 comprises a memory 216 and the processor 212. The memory 216 comprises the filter bank consisting's of a plurality of frequencies in the range of about 0 Hertz to 1000 Hertz.

The processor 212 is configured to analyze the accelerometry data to provide muscular activity data, based on which, the neural activity data is measured. Further, the processor 212 is configured to convert the accelerometry data to one or more frequencies. The processor 212 is configured to compare the converted one or more frequencies with the stored plurality of frequencies (stored in filter bank) to generate time-series data. The processor 212 is configured to analyze the generated time-series data for automatic detection of one or more neuro-cardiological disorders for comatose and non-comatose subject. Example of one or more neuro-cardiological disorders automatically detected based on accelerometry data comprise critical care myopathy, critical care polyneuropathy, encephalitis, encephalopathy and status epilepticus or combinations thereof At step 306, the processor 212 is configured to receive the first signal and the second signal from the data collector device 106 or directly from the wearable device 104. The data collector device 106 or the wearable device 104 is configured to transmit the first signal and the second signal to at least one base station and the at least one base station comprises a transceiver for receiving the first signal and the second signal. The first signal and the second signal are transmitted via the network 108.

At step 308, the processor 212 is configured to combine the first signal and the second signal to generate an output signal. In one example embodiment, the combination of the first signal and the second signal illustrates combining the heart-brain activity. For example, an algorithm is implemented that can combine the first signal and the second signal. For conciseness, the first signal and the second signal are independent component. The algorithm may be based on higher-level data augmentation using a Bayesian process.

In some embodiments, with reference to step 310, the I/O interface 214 is configured to display the output signal. The output signal is a graphical representation of a time-series data depicting one or more frequencies of the neural and heart activity. The one or more frequencies are utilized in acute stroke monitoring for the patient 102 with cardio vascular disease.

In one embodiment, with reference to step 312, the processor 212 is configured to identify one or more neuro-cardiological disturbances based on the displayed output signal. The processor 212 is configured to analyze the output signal to identify one or more neuro-cardiological disturbances for the one or more neuro-cardiological disorders. The one or more neuro-cardiological disorders comprise and are not limited to critical care myopathy, critical care polyneuropathy, delirium, hypoxic myoclonus, encephalitis, encephalopathy, systemic inflammatory response syndrome, status epilepticus or combinations thereof.

Figure 4:
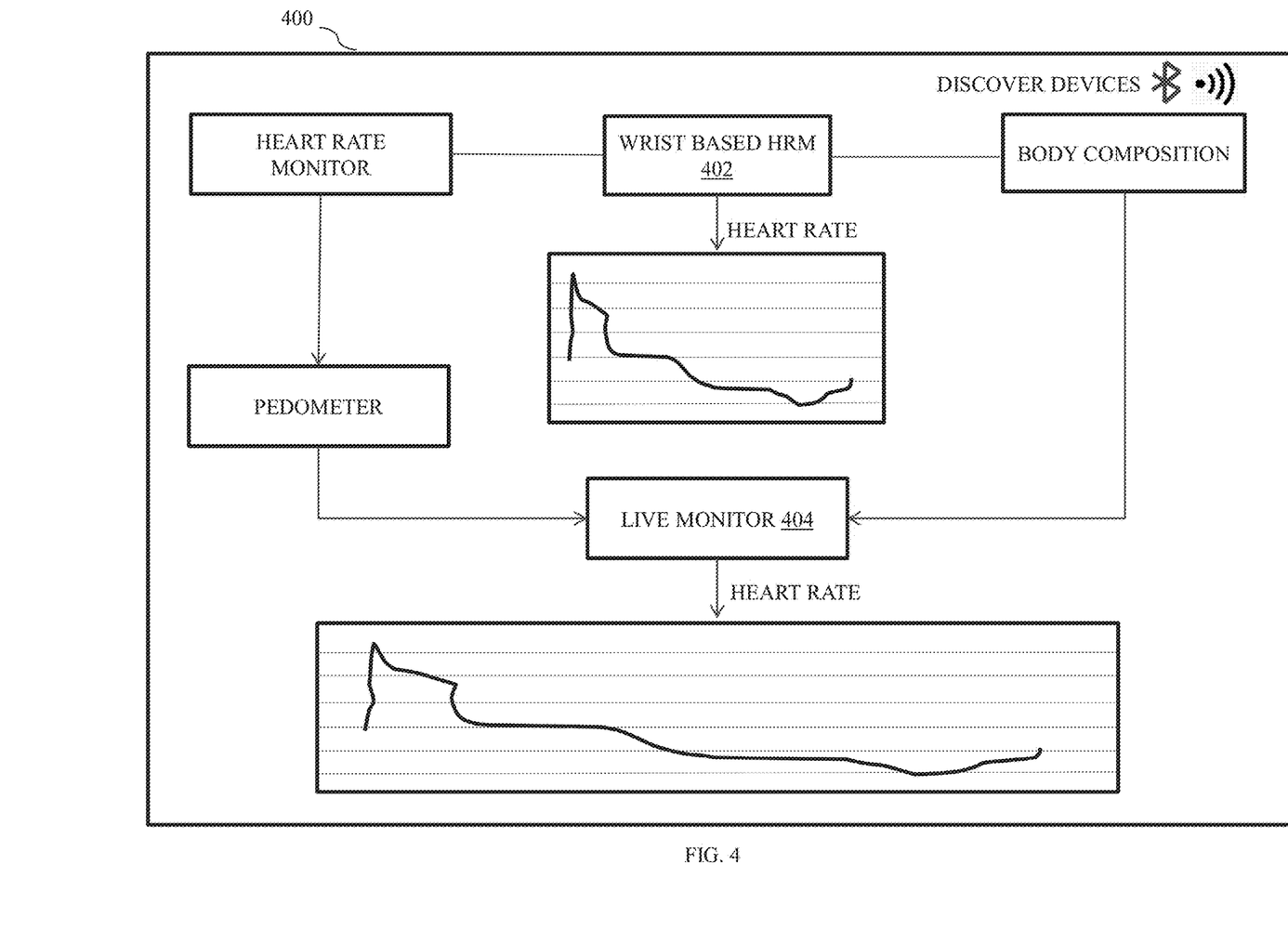
FIG. 4 illustrates an example user interface screen for allowing the control and display of many network enabled health monitoring devices on a single screen, according to an embodiment of the present disclosure.

FIG. 4 illustrates an example user interface screen 400 for allowing the control and display of many network enabled health monitoring devices on a single screen, according to an embodiment of the present disclosure. The screen 400 is divided into multiple discrete areas, called Device Controls and each area allows a specific network enabled health monitoring device control.

In one embodiment, the user interface screen illustrates the connection to a HRM (wearable device 104). When the HRM (wearable device 104) is in advertising mode the LED on the wrist watch will be flashing. When the desired device (wearable device 104) is selected from the list, the application of the example user interface screen 400 will form a connection to the device over (wearable device 104) a network (for example Bluetooth low energy). After connection, the device (wearable device 104) control will open fully and control over the device can begin. The periodic data reported by the wearable device 104 and the reporting of graphic data is indicated by flashing of LEDs. Periodic data is used only with the Wrist Based HRM device control.

In one embodiment, the HRM (wearable device 104) should be worn tightly around the wrist of the subject. The device is sensitive to motion. The quality of the output data is highly dependent on the stillness of the user's arm and placement of the sensor. The effect of motion can be visualized using the Live Monitor (404) device control. The graph shown in the Wrist Based HRM device control is a history of the reported values. The sub screen 402 shows up some measurement results.

Accordingly, the wearable device 104 provides monitoring of both, the heart and the brain activity of a subject in post-acute stroke period. The unique algorithm that can combine the monitoring of the the heart and the brain activity of a subject is disclosed herein. The algorithm is based on higher-level data augmentation using a Bayesian process. The use of the system 100 and the wearable device 104 in acute stroke monitoring is described herein.

While specific language has been used to describe the disclosure, any limitations arising on account of the same are not intended. As would be apparent to a person skilled in the art, various working modifications may be made to the method in order to implement the inventive concept as taught herein. The figures and the foregoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, orders of processes described herein may be changed and are not limited to the manner described herein. Moreover, the actions of any flow diagram need not be implemented in the order shown; nor do all of the acts necessarily need to be performed. Also, those acts that are not dependent on other acts may be performed in parallel with the other acts. The scope of embodiments is by no means limited by these specific examples. Numerous variations, whether explicitly given in the specification or not, such as differences in structure, dimension, and use of material, are possible. The scope of embodiments is at least as broad as given by the following claims.

We claim:

1. A system for monitoring a post-acute stroke subject for identifying one or more neuro-cardiological disturbances in the subject, the system comprising:
    a wearable device configured for capturing data associated with a neural activity and a heart activity, wherein the wearable device comprises:
        a first electrode and a second electrode configured for measuring an electrical activity of the subject's heart to generate a first signal representative of an ECG signal; and
        an accelerometer configured for detecting and acquiring motor accelerometry data of the subject for generating a second signal; and
    a processor with a memory, wherein the memory stores a plurality of modules for execution by the processor, and wherein the plurality of modules is configured for:
        receiving the first and the second signal from the wearable device;
        splitting the second signal into its predefined constituent frequency bands using a filter bank;
        combining the first signal and one or more constituent bands of frequencies of the second sound signal using a higher-level data augmentation based on at least one of a Bayesian process and a machine learning process, to generate one or more output signals; and
        identifying one or more neuro-cardiological disturbances based on the one or more output signals.

2. The system as claimed in claim 1, wherein the wearable device further comprises plurality of sensors configured for capturing data associated with the neural activity and heart activity of a subject in a post-acute stroke treatment and in the intensive care unit.

3. The system as claimed in claim 1, wherein the first electrode is placed at an under surface of the wearable device and adjacent to the radial artery permitting direct contact with the subject's ipsilateral wrist.

4. The system as claimed in claim 1, wherein the second electrode is placed on the outer surface of the wearable device and permitting direct contact with the subject's contralateral hand.

5. The system as claimed in claim 1, wherein the processor is configured to analyse the motor accelerometry data to provide muscular activity data, based on which, the neural activity data is measured.

6. The system as claimed in claim 1, wherein the processor is configured for comparing the one or more constituent bands of frequencies with the stored plurality of frequencies to generate time-series data.

7. The system as claimed in claim 6, wherein the processor is configured to analyse the generated time-series data for automatic detection of one or more neuro-cardiological disorders for monitoring a post-acute stroke subject.

8. The system as claimed in claim 7, wherein the one or more neuro-cardiological disorders automatically detected based on the generated time-series data comprise critical care myopathy, critical care polyneuropathy, encephalitis, encephalopathy and status epilepticus or combinations thereof.

9. The system as claimed in claim 1, wherein the processor is configured to analyse the output signal to identify one or more neuro-cardiological disturbances for the one or more neuro-cardiological disorders.

10. The system as claimed in claim 9, wherein the one or more neuro-cardiological disorders identified by the output signal comprise delirium, systemic inflammatory response syndrome or combinations thereof.

11. A method for monitoring a post-acute stroke subject for identifying one or more neuro-cardiological disturbances in a subject, the method comprising:
    capturing data associated with a neural activity and heart activity of the subject in a post-acute stroke treatment, wherein steps for capturing data associated with the neural and heart activity comprise:
        measuring an electrical activity of a heart to generate a first signal representative of an ECG signal; and
        detecting and acquiring motor accelerometry data of the subject to generate a second signal;
    receiving the first and the second signal;
    splitting the second signal into its predefined constituent frequency bands using a filter bank;
    combining the first signal and one or more constituent bands of frequencies of the second sound signal using a higher-level data augmentation based on at least one of a Bayesian process and machine learning process, to generate one or more output signals; and
    identifying one or more neuro-cardiological disturbances based on the one or more output signals.

12. The method as claimed in claim 11, comprising analysing the motor accelerometry data for providing muscular activity data based on which, the neural activity data is measured.

13. The method as claimed in claim 11, comprising comparing the one or more constituent bands of frequencies with a stored plurality of frequencies for generating time-series data.

14. The method as claimed in claim 13, comprising analysing the generated time-series data for automatically detecting a one or more neuro-cardiological disorders for monitoring a post-acute stroke subject.

15. The method as claimed in claim 14, wherein the one or more neuro-cardiological disorders automatically detected based on the generated time-series data comprise critical care myopathy, critical care polyneuropathy, encephalitis, encephalopathy and status epilepticus or combinations thereof.

16. The method as claimed in claim 11, comprising analysing the output signal for identifying one or more neuro-cardiological disturbances for the one or more neuro-cardiological disorders.

17. The system as claimed in claim 16, wherein the one or more neuro-cardiological disorders identified by the output signal comprise delirium, systemic inflammatory response syndrome or combinations thereof.

* * * * *